United States Patent
Ihara (10) Patent No.: US 10,846,853 B2
(45) Date of Patent: Nov. 24, 2020

(54) MEDICAL IMAGE PROCESSING APPARATUS, MEDICAL IMAGE PROCESSING METHOD, AND MEDICAL IMAGE PROCESSING PROGRAM

(71) Applicant: FUJIFILM Corporation, Tokyo (JP)

(72) Inventor: Satoshi Ihara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 77 days.

(21) Appl. No.: 15/948,266

(22) Filed: Apr. 9, 2018

(65) Prior Publication Data

US 2018/0300878 A1    Oct. 18, 2018

(30) Foreign Application Priority Data

Apr. 12, 2017 (JP) .............................. JP2017-078659

(51) Int. Cl.
*G06T 7/00* (2017.01)
*G06K 9/20* (2006.01)
(Continued)

(52) U.S. Cl.
CPC .......... *G06T 7/0014* (2013.01); *A61B 5/7264* (2013.01); *G06K 9/2054* (2013.01);
(Continued)

(58) Field of Classification Search
CPC ....... G06T 7/0014; G06T 15/06; G06T 15/20; G06T 7/0012; G06T 2207/10072; G06T 2207/20081; G06T 2207/20084; G06T 2207/30064; G06T 2207/30096; G06T 2207/30101; A61B 5/7264; A61B 5/055; A61B 6/032; A61B 8/0825; A61B 6/00; A61B 6/463; G06K 9/6267; G06K 9/2054;
(Continued)

(56) References Cited

U.S. PATENT DOCUMENTS

| 5,881,124 A | 3/1999 | Giger et al. |
| 2004/0151356 A1 | 8/2004 | Li et al. |

(Continued)

FOREIGN PATENT DOCUMENTS

| JP | 10-500321 A | 1/1998 |
| JP | 2013-537445 A | 1/1998 |

(Continued)

OTHER PUBLICATIONS

Tree-in-Bud Pattern, Rossi et al, 2005 https://pubs.rsna.org/doi/pdf/10.1148/rg.253045115 (Year: 2005).*

(Continued)

*Primary Examiner* — Jianxun Yang
(74) *Attorney, Agent, or Firm* — Birch, Stewart, Kolasch & Birch, LLP (57) ABSTRACT

The medical image processing apparatus includes a medical image acquisition unit that acquires a medical image; and a lesion detection unit that detects a lesion region in the medical image. The lesion detection unit includes a first identifier that identifies a lesion region candidate in the medical image and a second identifier that identifies whether the lesion region candidate identified by the first identifier is a blood vessel region, and detects the lesion region candidate that is not identified as the blood vessel region by the second identifier as the lesion region.

10 Claims, 4 Drawing Sheets

(51) Int. Cl.
*G06K 9/62* (2006.01)
*G06K 9/46* (2006.01)
*A61B 5/00* (2006.01)
*A61B 6/03* (2006.01)
*A61B 5/055* (2006.01)
*A61B 6/00* (2006.01)
*A61B 6/12* (2006.01)

(52) U.S. Cl.
CPC ......... *G06K 9/4604* (2013.01); *G06K 9/4628* (2013.01); *G06K 9/6232* (2013.01); *G06K 9/6271* (2013.01); *G06T 7/0012* (2013.01); *A61B 5/055* (2013.01); *A61B 6/032* (2013.01); *A61B 6/12* (2013.01); *A61B 6/5211* (2013.01); *G06K 2209/05* (2013.01); *G06K 2209/053* (2013.01); *G06T 2207/10072* (2013.01); *G06T 2207/10081* (2013.01); *G06T 2207/10088* (2013.01); *G06T 2207/20081* (2013.01); *G06T 2207/20084* (2013.01); *G06T 2207/30064* (2013.01); *G06T 2207/30096* (2013.01); *G06T 2207/30101* (2013.01)

(58) Field of Classification Search
CPC ............... G06K 9/4604; G06K 9/6232; G06K 2209/053
See application file for complete search history.

(56) References Cited

U.S. PATENT DOCUMENTS

| | | | |
|---|---|---|---|
| 2005/0107695 A1* | 5/2005 | Kiraly | G06T 15/06 600/431 |
| 2006/0120608 A1* | 6/2006 | Luo | A61B 8/0825 382/224 |
| 2006/0280347 A1* | 12/2006 | Shirahata | A61B 6/00 382/128 |
| 2013/0121548 A1 | 5/2013 | Kovalan et al. | |
| 2013/0243244 A1 | 9/2013 | Miyamoto et al. | |
| 2015/0379709 A1 | 12/2015 | Liang et al. | |
| 2017/0277977 A1* | 9/2017 | Kitamura | G06K 9/6267 |

FOREIGN PATENT DOCUMENTS

| | | |
|---|---|---|
| JP | 2006-521118 A | 9/2006 |
| JP | 2008-104886 A | 5/2008 |
| JP | 2009-211138 A | 9/2009 |
| JP | 2011-118543 A | 6/2011 |
| JP | 2013-192624 A | 9/2013 |
| JP | 2016-39874 A | 3/2016 |

OTHER PUBLICATIONS

Japanese Office Action for corresponding Japanese Application No. 2017-078659, dated Jul. 28, 2020, with English translation.

* cited by examiner

MEDICAL IMAGE PROCESSING APPARATUS, MEDICAL IMAGE PROCESSING METHOD, AND MEDICAL IMAGE PROCESSING PROGRAM

CROSS-REFERENCE TO RELATED APPLICATION

This application claims priority from Japanese Patent Application No. 2017-078659, filed on Apr. 12, 2017, the disclosure of which is incorporated by reference herein in its entirety.

BACKGROUND

Field of the Invention

The present invention relates to a medical image processing apparatus, a medical image processing method, and a medical image processing program that detect a lesion region included in a medical image.

Related Art

In recent years, according to advances in medical equipment such as a computed tomography apparatus (CT) or a magnetic resonance imaging apparatus (MRI), a high-quality and high-resolution three-dimensional image has been used in image diagnosis.

In this regard, a diffusive lung disease is known as a lung disease. The diffusive lung disease shows a characteristic pattern on a sectional image captured by a CT apparatus, or the like. Accordingly, it is effective to detect the diffusive lung disease using an identifier generated through machine learning.

However, for example, in the case of a tree-in-bud appearance (TIB) (spotted shadow or granular shadow), since the TIB shows a spotted pattern on a two-dimensional sectional image, it is difficult to distinguish between the TIB and a section of a blood vessel.

Thus, in order to distinguish between the TIB and the blood vessel, a technique that uses an identifier generated through machine learning in a three-dimensional image may be considered.

However, in the case of a diffusive lung disease, there are many cases where the diffusive lung disease is imaged with a thick slice thickness of 5 mm or larger, and it is very difficult to collect three-dimensional correct answer data to be used in machine learning, which is not practically usable.

JP2006-521118A discloses a method for extracting a nodule and a blood vessel using a three-dimensional emphasis filter, but it is difficult to collect three-dimensional images other than a three-dimensional image with a thick slice thickness as a three-dimensional image of a lung disease as described above, and thus, it is difficult to configure a highly accurate filter as a three-dimensional emphasis filter.

SUMMARY

In consideration of the above-mentioned problems, an object of the invention is to provide a medical image processing apparatus, a medical image processing method, and a medical image processing program capable of detecting a lesion such as a diffusive lung disease with high accuracy to be distinguished from a blood vessel.

According to an aspect of the invention, there is provided a medical image processing apparatus comprising: a medical image acquisition unit that acquires a medical image; and a lesion detection unit that detects a lesion region in the medical image, in which the lesion detection unit includes a first identifier that identifies a lesion region candidate in the medical image and a second identifier that identifies whether the lesion region candidate identified by the first identifier is a blood vessel region or whether the lesion region candidate is a bronchial region, and detects the lesion region candidate that is not identified as the blood vessel region or the bronchial region by the second identifier as the lesion region.

In the medical image processing apparatus according to this aspect of the invention, the first identifier may identify the lesion region candidate a two-dimensional medical image, and the second identifier may identify whether the lesion region candidate is the blood vessel region or whether the lesion region candidate is the bronchial region, using a three-dimensional medical image.

In the medical image processing apparatus according to this aspect of the invention, the first identifier may be machine-learned using a two-dimensional learning medical image data, and the second identifier may be machine-learned using a three-dimensional learning medical image data.

In the medical image processing apparatus according to this aspect of the invention, at least one of the first identifier or the second identifier may be machine-learned using a convolutional neural network (CNN).

In the medical image processing apparatus according to this aspect of the invention, the first identifier and the second identifier may be machine-learned using learning medical images having different slice thicknesses.

In the medical image processing apparatus according to this aspect of the invention, the first identifier may be machine-learned using a learning medical image having a slice thickness larger than that of a learning medical image of the second identifier.

In the medical image processing apparatus according to this aspect of the invention, the lesion region may be a lesion region of a tumor or a lesion region of a diffusive lung disease.

In the medical image processing apparatus according to this aspect of the invention, the lesion detection unit may store a reference slice thickness in advance, and may perform only the identification of the lesion region candidate in the first identifier to detect the lesion region candidate as the lesion region in a case where the medical image is an image having a slice thickness that is equal to or larger than the reference slice thickness.

In the medical image processing apparatus according to this aspect of the invention, the lesion detection unit may perform only the identification of the lesion region candidate in the first identifier to detect the lesion region candidate as the lesion region in a case where the medical image is only one sectional image.

According to another aspect of the invention, there is provided a medical image processing method comprising: acquiring a medical image, identifying a lesion region candidate in the medical image using a first identifier, and identifying whether the lesion region candidate identified by the first identifier is a blood vessel region or whether the lesion region candidate is a bronchial region, using a second identifier; and detecting the lesion region candidate that is not identified as the blood vessel region or the bronchial region by the second identifier as the lesion region.

According to still another aspect of the invention, there is provided a medical image processing program that causes a computer to function as: a medical image acquisition unit that acquires a medical image; and a lesion detection unit that detects a lesion region in the medical image, in which the lesion detection unit includes a first identifier that identifies a lesion region candidate in the medical image and a second identifier that identifies whether the lesion region candidate identified by the first identifier is a blood vessel region or whether the lesion region candidate is a bronchial region, and detects the lesion region candidate that is not identified as the blood vessel region or the bronchial region by the second identifier as the lesion region.

According to still another aspect of the invention, there is provided a medical image processing apparatus comprising: a memory that stores a command to be executed in a computer; and a processor configured to execute the stored command, in which the processor executes a process of acquiring a medical image and identifying a lesion region candidate in the medical image using a first identifier, a process of identifying whether the lesion region candidate identified by the first identifier is a blood vessel region or whether the lesion region candidate is a bronchial region, using a second identifier; and a process of detecting the lesion region candidate that is not identified as the blood vessel region or the bronchial region by the second identifier as the lesion region.

According to the medical image processing apparatus, the medical image processing method, and the medical image processing program according to the invention, a medical image is acquired, and a lesion region candidate in the medical image is identified using a first identifier. Further, whether the lesion region candidate identified by the first identifier is a blood vessel region or whether the lesion region candidate is a bronchial region is identified by a second identifier, and a lesion region candidate that is not identified as the blood vessel region or the bronchial region using the second identifier is detected as a lesion region. Thus, it is possible to detect a lesion region of a diffusive lung disease or the like with high accuracy to be distinguished from a blood vessel region.

DETAILED DESCRIPTION

Figure 1:
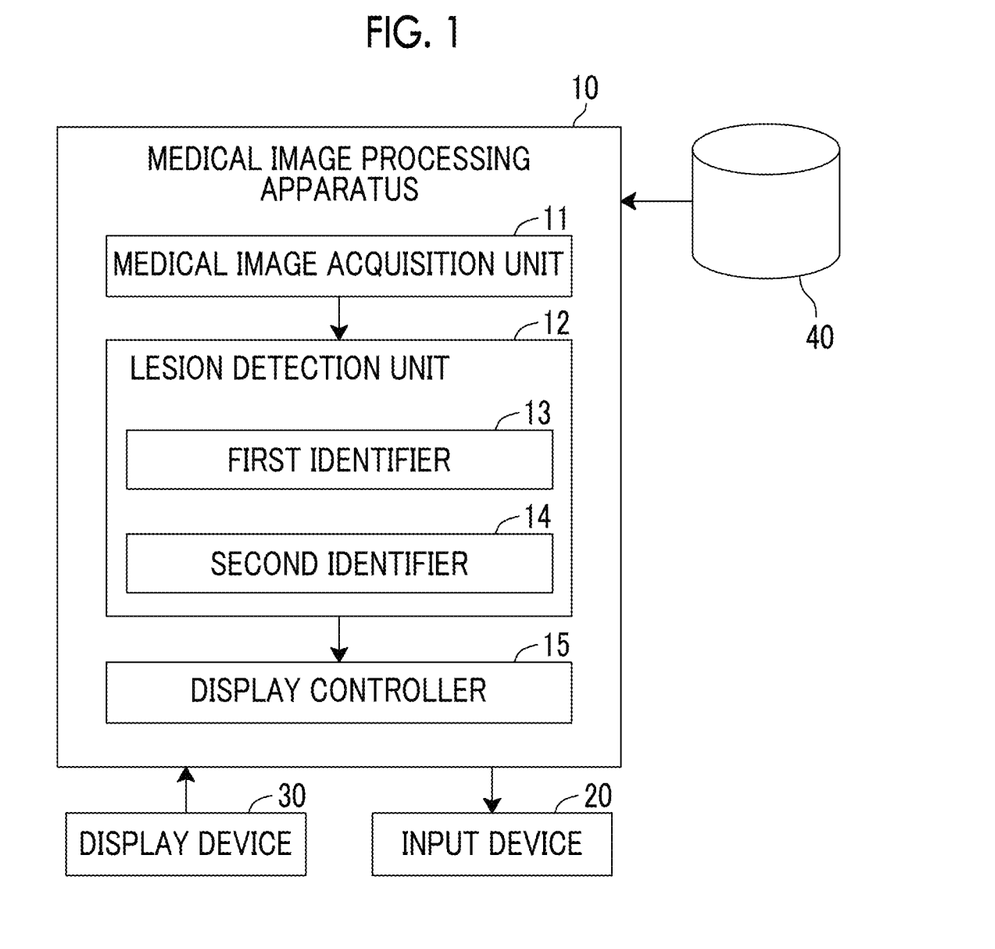
FIG. 1 is a block diagram showing a schematic configuration of a medical image diagnosis support system using an embodiment of a medical image processing apparatus according to the invention.

Hereinafter, a medical image diagnosis support system using an embodiment of a medical image processing apparatus, a medical image processing method, and a medical image processing program of the invention will be described in detail with reference to the accompanying drawings. FIG. 1 is a block diagram showing a schematic configuration of a medical image diagnosis support system according to an embodiment.

The medical image diagnosis support system according to this embodiment includes a medical image processing apparatus 10, a display device 20, an input device 30, and a three-dimensional image storage server 40, as shown in FIG. 1.

The medical image processing apparatus 10 is configured by installing a medical image processing program according to the embodiment into a computer. The medical image processing program may be recorded on a recording medium such as a digital versatile disc (DVD) or a compact disc read only memory (CD-ROM) for distribution, and may be installed into the computer from the recording medium. Alternatively, the medical image processing program may be stored in a storage device of a server computer connected to a network or a network storage in a state of being accessible from the outside, and may be downloaded and installed into a computer to be used by a doctor as necessary.

The medical image processing apparatus 10 includes a central processing unit (CPU), and a storage device such as a semiconductor memory, a hard disk or a solid state drive (SSD), and the like, and through the hardware, a medical image acquisition unit 11, a lesion detection unit 12, and a display controller 15 are configured, as shown in FIG. 1. Further, as the medical image processing program installed in the storage device is executed by the CPU, the respective units are operated, respectively. The medical image processing apparatus 10 is not configured using only a general-purpose CPU, but may be also configured using an application specific integrated circuit (ASIC), a field-programmable gate array (FPGA), or the like for a specific usage.

The medical image acquisition unit 11 acquires medical images of a test object that is imaged in advance before an operation or before an inspection, for example. As the medical images, a three-dimensional image configured by a plurality of sectional images output from a CT apparatus, a magnetic resonance imaging (MRI) apparatus, and the like, a three-dimensional image output from a multi slice (MS) CT apparatus and a cone beam CT apparatus, and the like may be used. The medical images are stored in advance together with test object identification information in the three-dimensional image storage server 40, and the medical image acquisition unit 11 reads out and acquires medical images corresponding to test object identification information input through the input device 30 from the three-dimensional image storage server 40.

The lesion detection unit 12 detects a lesion region included in the medical images acquired by the medical image acquisition unit 11. As the lesion region, there is a lesion region of a diffusive lung disease, a lesion region of a tumor, or the like. As the diffusive lung disease, for example, there is a TIB, or the like.

Figure 2:
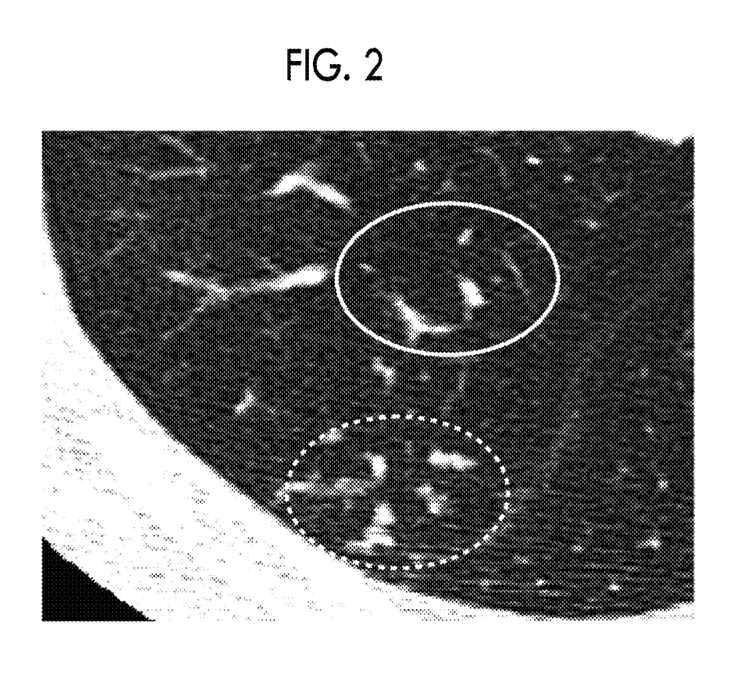
FIG. 2 is a diagram showing an example of a sectional image including TIBs and blood vessels.

Here, since the lesion of the diffusive lung disease or the like shows a characteristic pattern on a medical image, it is effective to detect the lesion using an identifier generated through machine learning. However, for example, in the case of a dot-like lesion such as a TIB, it is difficult to distinguish the dot-like lesion from a section of a blood vessel on a two-dimensional sectional image. FIG. 2 is a diagram showing an example of a sectional image including TIBs and blood vessels, in which a white pattern in a solid line ellipse represents a blood vessel pattern, and a white pattern in a broken line ellipse represents a TIB pattern. Here, it can be understood that both the patterns are extremely similar to each other.

Figure 3A:
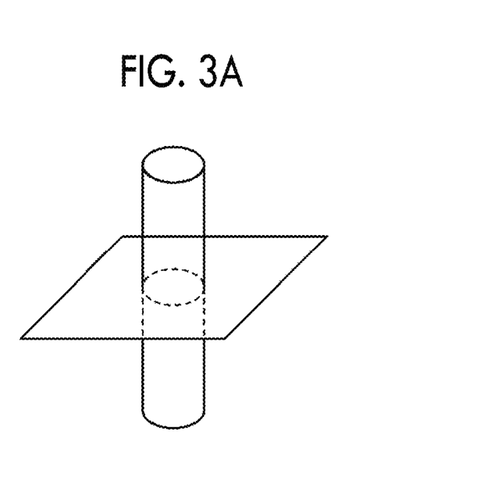
FIG. 3A is a diagram schematically showing a relationship between a traveling direction of a blood vessel and a sectional image.
Figure 3B:
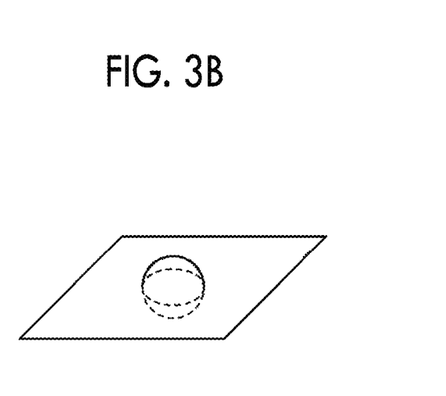
FIG. 3B is a diagram schematically showing a relationship between a TIB and a sectional image.

FIG. 3A is a diagram schematically showing a relationship between a traveling direction of a blood vessel (circular column) and a sectional image (plane), and FIG. 3B is a diagram schematically showing a relationship between a TIB (sphere) and a sectional image (plane). As shown in FIG. 3A, in a case where a blood vessel travels in a vertical direction or in a direction close to the vertical direction with respect to a sectional direction of the sectional image, a section in a direction orthogonal to the traveling direction of the blood vessel appears on the sectional image, which becomes a pattern that is similar to a circle. On the other hand, as shown in FIG. 3B, the TIB has a shape similar to a sphere, and thus, also shows a pattern similar to a circle on the sectional image. That is, since the blood vessel and the TIB appear as patterns similar to a circle on a sectional image, it is difficult to distinguish between the blood vessel and the TIB using, a single identifier.

Thus, in order to distinguish between the TIB and the blood vessel as described above, a technique that uses an identifier generated through machine learning in a three-dimensional image may be considered.

However, in the case of a diffusive lung disease, there are many cases where the diffusive lung disease is imaged with a thick slice thickness of 5 mm or larger, and it is very difficult to collect three-dimensional correct answer data to be used in machine learning, which is not practically usable.

On the other hand, even in a case where the pattern of the diffusive lung disease itself is not suitable machine learning as described above, as long as the fact that the pattern represents a blood vessel is identifiable, it is possible to correct misrecognition of machine learning in two dimensions. Since a blood vessel has nothing to do with a lung disease, it is possible to easily collect a three-dimensional image with a thin slice thickness, and thus, it is possible to create many pieces of correct answer data.

The lesion detection unit 12 of this embodiment is configured from the above-described viewpoint, and includes two identifiers of a first identifier 13 and a second identifier 14. The first identifier 13 identifies a lesion region candidate in a medical image.

The first identifier 13 is an identifier, configured of a multilayered neural network, generated by deep learning that is machine learning. As the multilayered neural network, a convolutional neural network (CNN) is preferably used. Here, the invention is not limited thereto, and other known methods such as AdaBoost or a support vector machine (SVM) may be used.

In the multilayered neural network, a computation process is performed in each layer using various kernels with respect to data on a plurality of different feature values obtained through a previous-stage layer. Then, by further performing a computation process in a next-stage layer and subsequent layers with respect to the data on the feature values obtained by the former computation process, it is possible to improve a recognition rate of the feature values, and to classify the input data into a plurality of classes.

Figure 4:
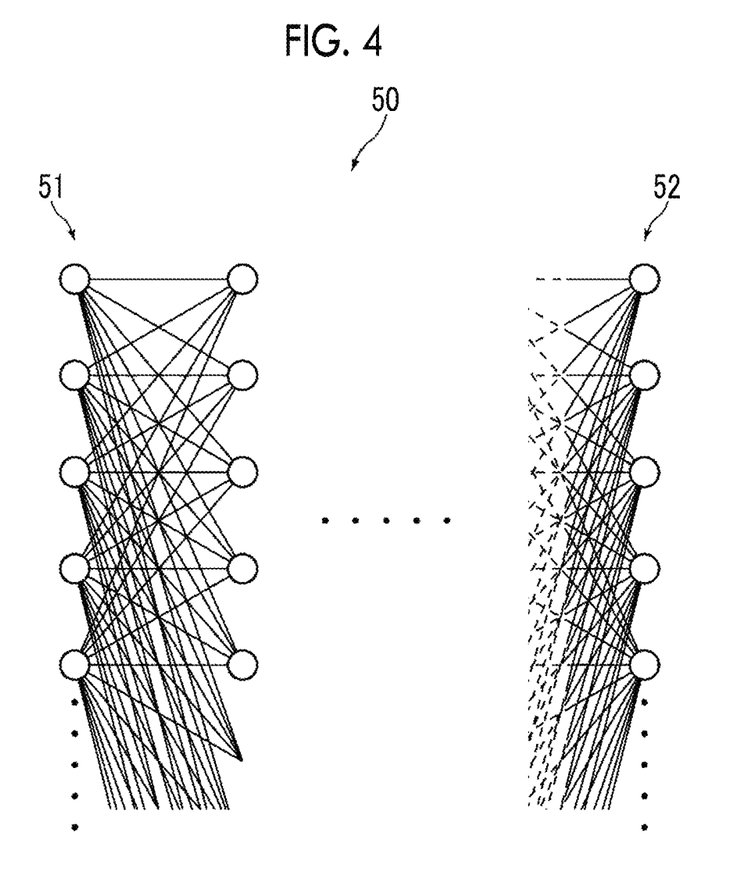
FIG. 4 is a diagram showing an example of a multilayered neural network.
Figure 5:
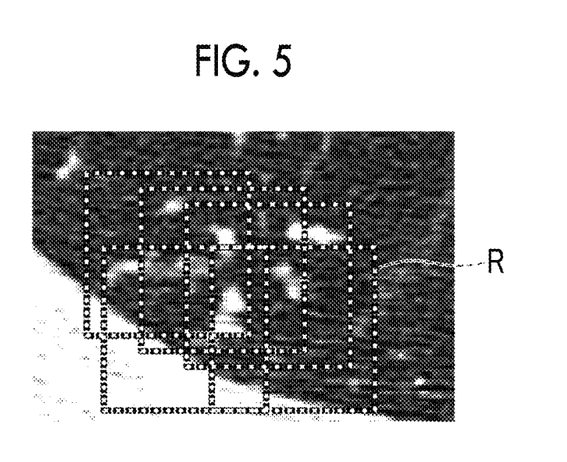
FIG. 5 is a diagram for illustrating machine learning of a first identifier.

FIG. 4 is a diagram showing an example of such a multilayered neural network. As shown in FIG. 4, a multi-layered neural network 50 includes a plurality of layers including an input layer 51 and an output layer 52. In this embodiment, learning is performed using teacher data of TIB in the multilayered neural network 50. In the learning, as shown in FIG. 5, a region-of-interest R of a predetermined size (for example, 1.5 cm×1.5 cm) is cut from a two-dimensional sectional image (corresponding to a two-dimensional learning medical image data of the invention) for which it is known that a TIB region is included therein, and the region-of-interest R is used as teacher data. Further, the teacher data is input to the multilayered neural network 50, and a result indicating the presence or absence of the TIB region is output therefrom. Then, the output result is compared with the teacher data, and according to whether its answer is correct or incorrect, coupling weights, between respective layers, of units (indicated by circles in FIG. 4) included in each layer of the multilayered neural network 50 are corrected toward an input side from an output side. The correction of the coupling weights is repeated by a predetermined number of times or until a correct answer rate of the output classification result reaches 100% using the multiple pieces of teacher data, and then, the machine learning is terminated.

Further, since machine learning is performed using a two-dimensional sectional image with respect to the first identifier 13 as described above, even though the slice thickness of the sectional image is thick, there is no particular problem. Accordingly, it is possible to use a sectional image having a thickness of 5 mm imaged in many hospitals, and thus, it is possible to collect a large amount of TIB correct answer data, and to enhance identification accuracy of the first identifier 13. Here, it is preferable that the number of sectional images used in machine learning is large, but even one sectional image may also be used.

Further, in a case where identification of a lesion region candidate is performed, a region-of-interest having the same size as that of teacher data is sequentially cut from each sectional image of a three-dimensional image that is an identification target, and the region-of-interest is input to the first identifier 13. Then, with respect to a central pixel of the cut region-of-interest, an identification result indicating whether the central pixel is a pixel that belongs to a TIB region is output. Thus, with respect to all pixels included in the sectional image, identification results indicating whether the pixels are pixels that belong to the TIB region is output. However, as described above, since a TIB and a blood vessel show similar patterns on a sectional image, even pixels that belong to a blood vessel region are identified as pixels that belong to a TIB region. Accordingly, the first identifier 13 identifies the pixels that belong to the TIB region included in the sectional image and the pixels that belong to the blood vessel region as pixels of the lesion region candidate.

Next, the second identifier 14 will be described. The second identifier 14 identifies whether a lesion region candidate identified by the first identifier 13 corresponds to a blood vessel region. The second identifier 14 according to this embodiment is an identifier configured of a multilayered neural network, similar to the first identifier 13. As the multilayered neural network, a CNN is preferably used. Here, the invention is not limited thereto, and other known methods such as AdaBoost or an SVM may be used.

Further, the second identifier 14 is also generated through machine learning, similar to the first identifier 13, but as teacher data on an input side, a three-dimensional image (corresponding to a three-dimensional learning medical image data of the invention) for which it is known that a blood vessel region is included therein may be used. Specifically, a region-of-interest is cut with respect to each of a plurality of sectional images that form the three-dimensional image, and the region-of-interest is used as teacher data, and thus, machine learning in the three-dimensional image is performed. It is preferable that the slice thickness of sectional images used as teacher data of the second identifier 14 is thinner than the slice thickness of sectional images used as teacher data of the first identifier 13. In the case of a blood vessel region, a large amount of correct answer data of a three-dimensional image imaged with a slice thickness thinner than that in a TIB region can also be obtained, it is possible to sufficiently secure the accuracy of the second identifier 14.

In this embodiment, machine learning is performed using a two-dimensional sectional image with respect to the first identifier 13, but the invention is not limited thereto, and the machine learning may be performed using a three-dimensional image, similar to the second identifier 14.

Further, in a case where identification of a blood vessel region is performed, a lesion region candidate of each sectional image identified by the first identifier 13 is input to the second identifier 14 as a three-dimensional lesion region candidate. The second identifier 14 cuts a three-dimensional region-of-interest from the three-dimensional lesion region candidate, and identifies whether a central pixel of the region-of-interest is a pixel that belongs to a blood vessel region.

In addition, the second identifier 14 identifies whether all pixels of the lesion region candidate are pixels that belong to a blood vessel region, and the lesion detection unit 12 detects a lesion region candidate that includes a pixel group identified as the pixels that belong to the blood vessel region as the blood vessel region, and detects a lesion region candidate that includes a pixel group identified as pixels that are not the pixels that belong to the blood vessel region as a lesion region.

Returning to FIG. 1, the display controller 15 allocates a color to each sectional image that is an identification target or a three-dimensional image on the basis of a lesion region detected by the lesion detection unit 12 to generate a mapping image, and displays the mapping image on the display device 20.

Further, the display controller 15 is capable of displaying a three-dimensional image or each sectional image acquired by the medical image acquisition unit 11, an identification result of a lesion region candidate in the first identifier 13, and the like on the display device 20.

The display device 20 includes, a liquid crystal display, or the like. Further, the display device 20 may be configured of a touch panel, and may be commonly used as the input device 30.

The input device 30 includes a mouse, a keyboard, or the like, and receives various setting inputs from a user. Specifically, for example, the input device 30 receives a setting input of identification information on a patient, or the like.

Figure 6:
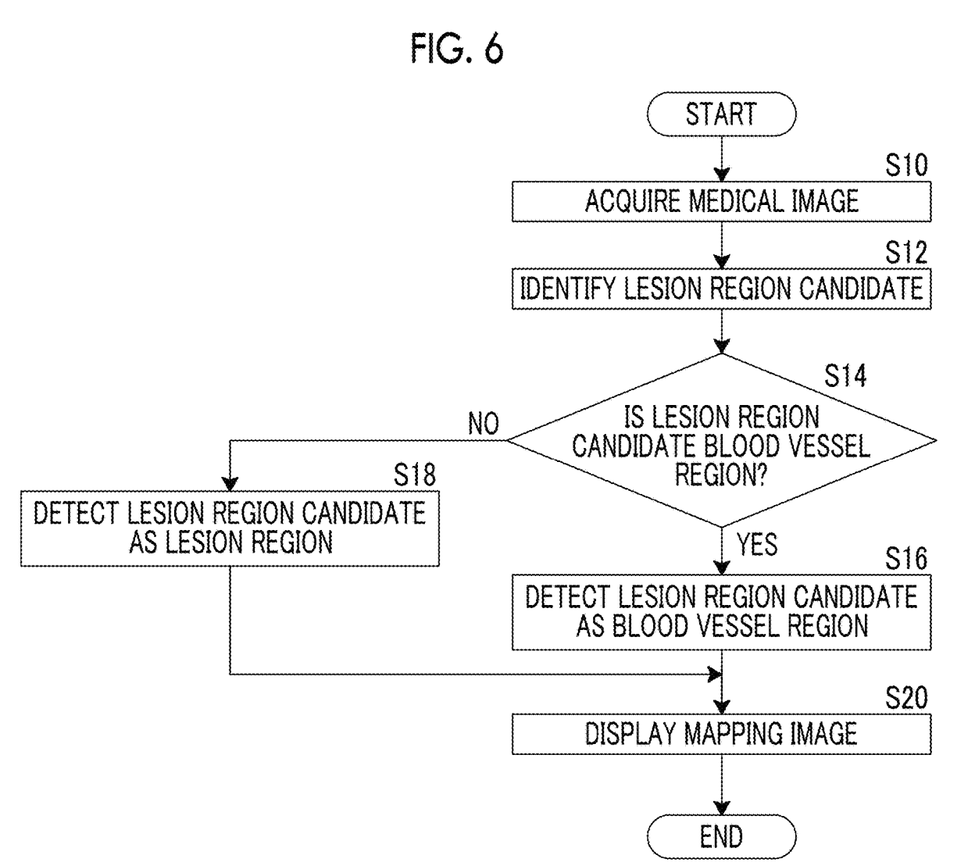
FIG. 6 is a flowchart for illustrating an operation of a medical image diagnosis support system using an embodiment of a medical image processing apparatus according to the invention.

Next, an operation of a medical image diagnosis support system according to this embodiment will be described with reference to a flowchart shown in FIG. 6.

First, a medical image of a patient is acquired according to a setting input of identification information on the patient or the like from a user (S10).

Respective sectional images that form the medical image are output to the first identifier 13, and the first identifier 13 identifies whether each pixel of each input sectional image is a pixel that belongs to a lesion region candidate (S12).

Further, a lesion region candidate of each sectional image identified by the first identifier 13 is input to the second identifier 14 as a three-dimensional lesion region candidate. The second identifier 14 identifies whether each pixel of the three-dimensional lesion region candidate is a pixel that belongs to a blood vessel region (S14).

In addition, the lesion detection unit 12 detects a lesion region candidate that includes a pixel group identified as the pixels that belong to the blood vessel region as the blood vessel region (S16), and detects a lesion region candidate that includes a pixel group identified as pixels that are not the pixels that belong to the blood vessel region as a lesion region (S18).

Furthermore, the display controller 15 generates a mapping image on the basis of the lesion region detected by the lesion detection unit 12, and displays the mapping image on the display device 20 (S20).

According to the medical image diagnosis support system according to the above-described embodiment, a lesion region candidate in a medical image is identified using the first identifier 13, whether the lesion region candidate identified by the first identifier 13 is a blood vessel region is identified by the second identifier 14, and the lesion region candidate that is not identified as the blood vessel region by the second identifier 14 is detected as a lesion region. Thus, it is possible to detect a lesion region of a diffusive lung disease or the like with high accuracy to be distinguished from a blood vessel region.

In the above-described embodiment, identification of a lesion region candidate is performed using the first identifier 13, and then, identification using the second identifier 14 is performed to detect a lesion region, but in a case where the slice thickness of a sectional image that is an identification target is thick, there is a case where it is difficult to perform identification with high accuracy even in a case where identification of a three-dimensional blood vessel region is performed using the second identifier 14.

Accordingly, in the lesion detection unit 12, a reference slice thickness is stored in advance, and in a case where the slice thickness of an input sectional image is equal to greater than the reference slice thickness, only identification of a lesion region candidate may be performed using the first identifier 13 to detect the lesion region candidate as a lesion region. As the reference slice thickness, a thickness of 5 mm obtained by imaging in many hospitals is preferably used.

Further, since the second identifier 14 identifies a three-dimensional blood vessel region as described above, in a case where a medical image that is an identification target is only one sectional image, it is not possible to identify a blood vessel region.

Accordingly, in the lesion detection unit 12, in a case where a medical image that is an identification target is only one sectional image, only identification of a lesion region candidate may be performed using the first identifier 13 to detect the lesion region candidate as a lesion region.

In addition, in the above-described embodiment, the second identifier 14 identifies whether a lesion region candidate identified by the first identifier 13 is a blood vessel region, but the invention is not limited thereto. For example, the second identifier 14 may identify whether the lesion region candidate is a bronchial region. In this case, the second identifier 14 is machine-learned using a three-dimensional image for which it is known that a bronchial region is included therein as teacher data. Further, a lesion region candidate that is not identified as a bronchial region by the second identifier 14 may be detected as a lesion region.

What is claimed is:
1. A medical image processing apparatus comprising:
  processing circuitry configured to:
    acquire a medical image, the medical image being a three-dimensional image; and
    detect a lesion region in the medical image, wherein a first identifier identifies a lesion region candidate in the medical image and a second identifier identifies whether the lesion region candidate identified by the first identifier is a blood vessel region or whether the lesion region candidate is a bronchial region, and the lesion region candidate that is not identified as the blood vessel region or the bronchial region by the second identifier is detected as the lesion region, wherein the first identifier is machine-learned using a two-dimensional learning medical image for which it is known that a lesion region is included therein as teacher data, wherein the second identifier is machine-learned using a three-dimensional learning medical image for which it is known that a blood vessel region or a bronchial region is included therein as teacher data, the three-dimensional learning medical image consisting of a plurality of sectional images, wherein the first identifier identifies the lesion region candidate using a two-dimensional region-of-interest, which is sectional image composed of the medical image, and wherein the second identifier identifies whether the lesion region candidate is the blood vessel region or whether the lesion region candidate is the bronchial region, using a three-dimensional region-of-interest, which consists of a plurality of regions-of-interest cut with respect to each of a plurality of sectional images that form the medical image, the three-dimensional region-of-interest including the two-dimensional region-of-interest.

2. The medical image processing apparatus according to claim 1,
wherein at least one of the first identifier or the second identifier is machine-learned using a convolutional neural network (CNN).

3. The medical image processing apparatus according to claim 1,
wherein the first identifier and the second identifier are machine-learned using learning medical images having different slice thicknesses.

4. The medical image processing apparatus according to claim 3,
wherein the first identifier is machine-learned using a learning medical image having a slice thickness larger than that of a learning medical image of the second identifier.

5. The medical image processing apparatus according to claim 1,
wherein the lesion region is a lesion region of a tumor or a lesion region of a diffusive lung disease.

6. The medical image processing apparatus according to claim 1,
wherein the processing circuitry is further configured to store a reference slice thickness in advance, and
performs only the identification of the lesion region candidate in the first identifier to detect the lesion region candidate as the lesion region in a case where the medical image is an image having a slice thickness that is equal to or larger than the reference slice thickness.

7. The medical image processing apparatus according to claim 1,
wherein the processing circuitry is further configured to perform only the identification of the lesion region candidate in the first identifier to detect the lesion region candidate as the lesion region in a case where the medical image is only one sectional image.

8. The medical image processing apparatus according to claim 1,
wherein the lesion region appears on the medical image as a tree-in-bud appearance.

9. A medical image processing method comprising:
acquiring a medical image, the medical image being a three-dimensional image, identifying a lesion region candidate in the medical image using a first identifier, and identifying whether the lesion region candidate identified by the first identifier is a blood vessel region or whether the lesion region candidate is a bronchial region, using a second identifier; and
detecting the lesion region candidate that is not identified as the blood vessel region or the bronchial region by the second identifier as the lesion region,
wherein the first identifier is machine-learned using a two-dimensional learning medical image for which it is known that a lesion region is included therein as teacher data,
wherein the second identifier is machine-learned using a three-dimensional learning medical image for which it is known that a blood vessel region or a bronchial region is included therein as teacher data, the three-dimensional learning medical image consisting of a plurality of sectional images,
wherein the first identifier identifies the lesion region candidate using a two-dimensional region-of-interest, which is sectional image composed of the medical image, and
wherein the second identifier identifies whether the lesion region candidate is the blood vessel region or whether the lesion region candidate is the bronchial region, using a three-dimensional region-of-interest, which consists of a plurality of regions-of-interest cut with respect to each of a plurality of sectional images that form the medical image, the three-dimensional region-of-interest including the two-dimensional region-of-interest.

10. A non-transitory computer-readable storage medium storing therein a medical image processing program that causes a computer to:
acquire a medical image, the medical image being a three-dimensional image; and
detect a lesion region in the medical image,
wherein a first identifier identifies a lesion region candidate in the medical image and a second identifier identifies whether the lesion region candidate identified by the first identifier is a blood vessel region or whether the lesion region candidate is a bronchial region, and the lesion region candidate that is not identified as the blood vessel region or the bronchial region by the second identifier is detected as the lesion region,
wherein the first identifier is machine-learned using a two-dimensional learning medical image for which it is known that a lesion region is included therein as teacher data,
wherein the second identifier is machine-learned using a three-dimensional learning medical image for which it is known that a blood vessel region or a bronchial region is included therein as teacher data, the three-dimensional learning medical image consisting of a plurality of sectional images,
wherein the first identifier identifies the lesion region candidate using a two-dimensional region-of-interest, which is sectional image composed of the medical image, and wherein the second identifier identifies whether the lesion region candidate is the blood vessel region or whether the lesion region candidate is the bronchial region, using a three-dimensional region-of-interest, which consists of a plurality of regions-of-interest cut with respect to each of a plurality of sectional images that form the medical image, the three-dimensional region-of-interest including the two-dimensional region-of-interest.

* * * * *